(12) United States Patent
Wilson (10) Patent No.: US 6,337,215 B1
(45) Date of Patent: Jan. 8, 2002

(54) MAGNETIC PARTICLES HAVING TWO ANTIPARALLEL FERROMAGNETIC LAYERS AND ATTACHED AFFINITY RECOGNITION MOLECULES

(75) Inventor: Robert John Wilson, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 08/982,019

(22) Filed: Dec. 1, 1997

(51) Int. Cl.$^7$ ...................... G01N 33/353; C12N 11/14; C12N 13/00; C07K 17/14

(52) U.S. Cl. ...................... 436/526; 210/222; 210/695; 252/62.51 R; 427/127; 435/7.1; 435/7.94; 435/173.1; 435/173.9; 435/176; 435/815; 436/524; 530/402; 530/403; 530/413; 530/811

(58) Field of Search ................................ 435/174, 176, 435/177, 180, 181, 7.1, 7.94, 173.1, 173.9, 261, 815; 436/518, 523, 524, 526, 528, 531, 533, 534; 530/810, 811, 812, 815, 816, 402, 403, 413; 252/62.51 R, 62.54; 427/127; 210/222, 695

(56) References Cited

U.S. PATENT DOCUMENTS

| | | | |
|---|---|---|---|
| 4,103,315 A | 7/1978 | Hempstead et al. ......... 360/110 |
| 4,169,804 A | 10/1979 | Yapel, Jr. ................. 252/62.53 |
| 4,336,173 A | 6/1982 | Ugelstad ..................... 523/205 |
| 4,452,773 A | 6/1984 | Molday ....................... 424/1.1 |
| 4,554,088 A | 11/1985 | Whitehead et al. ....... 252/65.54 |
| 4,710,472 A | 12/1987 | Saur et al. .................. 435/287 |
| 4,731,337 A | 3/1988 | Luotola et al. ............. 436/526 |
| 4,777,145 A | 10/1988 | Luotola et al. ............. 436/526 |
| 4,795,698 A | 1/1989 | Owen et al. .................... 435/4 |
| 4,891,725 A | 1/1990 | Mowry ....................... 360/113 |
| 4,910,148 A | 3/1990 | Sorensen et al. ........ 435/317.1 |
| 4,920,061 A | 4/1990 | Poynton et al. ............. 436/526 |
| 4,935,147 A | 6/1990 | Ullman et al. .............. 210/695 |
| 4,948,739 A | 8/1990 | Charmot ..................... 436/533 |
| 5,014,147 A | 5/1991 | Parkin et al. ............... 360/113 |
| 5,039,559 A | 8/1991 | Sang et al. ............... 252/62.51 |
| 5,076,950 A | 12/1991 | Ullman et al. ........... 427/213.3 |
| 5,081,030 A | 1/1992 | Civin ....................... 435/240.2 |
| 5,123,901 A | 6/1992 | Carew ............................ 604/5 |
| 5,145,784 A | 9/1992 | Cox et al. ................... 436/526 |
| 5,147,841 A | 9/1992 | Wilcoxon ................... 502/173 |
| 5,186,827 A | 2/1993 | Liberti et al. ............... 422/101 |
| 5,204,451 A | 4/1993 | Chang ........................ 530/413 |
| 5,219,577 A | 6/1993 | Kossovsky et al. ......... 424/494 |
| 5,238,815 A | 8/1993 | Higo et al. ................. 435/7.92 |
| 5,279,936 A | 1/1994 | Vorpahl ......................... 435/6 |
| 5,341,118 A | 8/1994 | Parkin et al. ............. 338/32 R |
| 5,341,261 A | 8/1994 | Dieny et al. ................ 360/113 |
| 5,374,531 A | 12/1994 | Jensen ........................ 435/7.24 |
| 5,436,778 A | 7/1995 | Lin et al. .................... 360/113 |
| 5,452,163 A | 9/1995 | Coffey et al. ............... 360/113 |
| 5,464,696 A | 11/1995 | Tournier et al. ............ 428/403 |
| 5,465,185 A | 11/1995 | Heim et al. ................. 360/113 |
| 5,466,574 A | 11/1995 | Liberti et al. .................. 435/5 |
| 5,491,068 A | 2/1996 | Benjamin et al. .......... 435/7.32 |
| 5,547,748 A | * 8/1996 | Auoff et al. ................. 428/323 |

OTHER PUBLICATIONS

L. Delmonte, SyStemix to Begin its Clinical–Scale Stem Cell Sorter Trials, *Genetic Engineering News* 15(4) Feb. 15, 1995.

Y. Gazitt, et al., Purified CDE4$^+$ Lin–Thy$^+$ Stem Cells Do Not Contain Clonal Myeloma Cells, *Blood*, 86(1):381–389, Jul. 1, 1995.

B. Haukanes et al., Applications of Magnetic Beads in Bioassays, *Bio/Technology* 11:60–63, Jan. 1993.

L. Joyce, From Holy Grail to Handy Gadget . . . Hematology to Work, *Standard Medicine*, 22–25, Winter 94/95.

J.P. Chen et al., Magnetic Properties of Microemulsion Synthesized Cobalt Fine Particles, *J. Appl. Phys.* 75(10):5876–5878, May 15, 1994.

S. Palacin, Patterning with Magnetic Materials at the Micron Scale, *Chem. Mater.* 8:1316–1325, 1996.

Dr. Reading, High–Speed Cell Sorter . . . Transplantation Patients, *Oncology News International*, 4(2), Feb. 1995.

W. Schutt et al., Applications of Magnetic Targeting . . . A Mini–Review, *Hybridoma*, 16(1):109–117, 1997.

B.D. Terris, et al., Nanoscale Replication for Scanning Probe Data Storage, *Appl. Phys. Lett.* 69(27):4262–4264, Dec. 30, 1996.

(List continued on next page.)

Primary Examiner—David M. Naff
(74) Attorney, Agent, or Firm—Thomas R. Berthold (57) ABSTRACT

Magnetic particles are prepared and used for selective separation of affinity bound partners in solution. The magnetic particles have large magnetic moments which can be made such that different strengths of magnetic moments and/or different magnetic field dependencies can be used to allow for separation of several affinity partners simultaneously. Magnetic particles having different magnetic moments and different attached acceptor molecules move at different rates in a magnetic field. The magnetic particles have a first ferromagnetic layer having a moment oriented in a first direction, a second ferromagnetic layer having a moment oriented in a second direction generally antiparallel to the first direction and a nonmagnetic spacer layer located between and in contact with the first and second ferromagnetic layers. The magnitude of the moment of the first ferromagnetic layer is substantially equal to the magnitude of the moment of the second ferromagnetic layer so that the magnetic particles have substantially zero net magnetic moment in the absence of an applied magnetic field. First and second antiferromagnetic layers may be in contact with and exchange coupled with the first and second ferromagnetic layers, respectively, for pinning the moments in the first and second directions. Affinity recognition molecules may be attached to a coating on the surface of the particles for selectively binding with a target molecule. When the recognition molecule is an antibody, the particles may be used in an immunoassay or to separate cells from a mixture by binding to cell surface antigens.

5 Claims, 7 Drawing Sheets

OTHER PUBLICATIONS

D. Zhang, et al., Synthesis of Nano–Scale Magnetic . . . of These Materials, *High Temperature and Materials Science*, 36:135–154, 1997.

Becton Dickinson Immunocytometry Systems, Product Catalog & Price List, 1995–1996.

SyStemix, Inc. Annual Report 1994.

SyStemix, 1995 Semiannual Report.

Dynabeads Biomagnetic Separation Products, 1996 Catalog.

\* cited by examiner

MAGNETIC PARTICLES HAVING TWO ANTIPARALLEL FERROMAGNETIC LAYERS AND ATTACHED AFFINITY RECOGNITION MOLECULES

RELATED APPLICATION

Application Ser. No. 09/153,985, filed Sep. 16, 1998, now U.S. Pat. No. 5,932,097, is a continuation of this application.

BACKGROUND OF THE INVENTION

1. Field of the Invention

This invention relates generally to magnetic particles, and in particular to a method for fabricating magnetic particles for applications to affinity binding.

2. Description of Related Art

Magnetic particle (also known as magnetic bead) techniques have been established as valuable tools in several areas of biotechnology. The efficacy of these techniques derives from the basic property that the beads may be chemically attached or conjugated to various biochemical molecules with selective target recognition capabilities (such as proteins and nucleic acids) and added to extremely complex reaction mixtures (such as whole blood or fragmented cells in solution) so that the resulting affinity bound complexes become magnetic entities. In separations these complexes are selectively captured by a magnetic field followed by removal of unwanted impurities. Other applications, which include spatial confinement and magnetically induced aggregate formation, also exist.

The uses of magnetic bead technologies in nucleic acid scientific research include purifications for sequencing DNA, for isolating expressed RNA or proteins in differentiating cell lines, for constructing differential c-DNA libraries, for sorting chromosomes and large DNA molecules, and for isolating DNA binding proteins. There is currently a very large medical effort at whole cell separations for treatments such as bone marrow transplantation and organ transplant tolerance generation.

One limitation associated with the present technology is that magnetic separation based on only a single target is carried out at a given time, making potential multiple separations difficult, time consuming, and expensive. Further, a second separation on a given subject may not achieve optimal results, because the errors of the separations may be additive. If sufficiently distinctive magnetic particles could be produced and coupled to distinct "recognition" molecules then it might be possible to separate the particles, and their bound targets, into different groups which reflect the type and number of bound magnetic particles. One example of the advantages offered by this capability is found in the literature pertaining to bone marrow transplantation. Here it found that separations based a single cell surface marker are routinely accomplished by magnetic bead techniques while separations based on multiple cell surface markers resort to fluorescence activated cell sorters which must analyze cells on an individual basis.

It can be seen, then, that there is a need for magnetic particles that have distinct and controllable magnetic properties and that can be attached to genetic material or other objects of interest.

SUMMARY OF THE INVENTION

To overcome the limitations in the prior art described above, and to overcome other limitations that will become apparent upon reading and understanding the present specification, the present invention discloses a method and apparatus for fabricating distinctive magnetic particles for affinity binding applications. The invention is discussed in detail for the application of biological separations, but is not limited to this application. The method comprises the steps of making a plurality of first magnetic beads having a first magnetic moment, making a plurality of second magnetic beads having a second magnetic moment, attaching a first acceptor molecule to the first magnetic beads, attaching a second acceptor molecule to the second magnetic beads, placing the first magnetic beads and the second magnetic beads into a solution, and applying an external magnetic field to the solution, whereby the first and second magnetic beads are caused to move at different rates by application of a magnetic field. The velocities of the beads depend upon viscous drag forces, the applied magnetic field and field gradient, and on the magnetic moments of the first and second magnetic beads, which may also depend on the magnetic field. Various advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there is illustrated and described specific examples in accordance with the invention.

BRIEF DESCRIPTION OF THE DRAWINGS

Referring now to the drawings in which like reference numbers represent corresponding parts throughout.

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

The use of magnetic particles or other markers to separate desired or undesired molecules, antigens, or antibodies from human blood or tissue is presently receiving enormous effort. The magnetic particles at one current focus of study are uniform, approximately 5 micron diameter, polystyrene spheres which are made superparamagnetic by including up to 35% (w/w) of magnetic iron oxides. Variants of the current state of the art include the use of a heterogeneous size distribution for the particles, the use of small (<0.1 micron) superparamagnetic particles, and the use of demagnetized ferromagnetic particles.

The application of magnetic bead technologies in medicine to separate intact cells uses the magnetic beads coated with monoclonal antibodies or other specific binding partners to cell surface antigens which allow cells with desirable properties to be purified from complex mixtures.

Generally such work involves cell surface protein markers, which are denoted by a Cluster of Differentiation nomenclature (e.g., CD21), that specifies the type of cells expressing each marker. Extensive commercial development and marketing of magnetic cell sorting equipment directing at monitoring, isolating and purifying various classes of lymphocytes of the immune system is presently underway.

Prominent efforts currently involve separating immune system stem cells (CD34), which primarily reside in bone marrow, and divide and differentiate to form all classes of cells involved in the immune response. The motivation behind this research is to isolate such cells from an individual or donor in order to repopulate the immune system of patients who have undergone radiation treatments or chemotherapy at dosages fatal to stem cells. Similar efforts are directed at removing cytotoxic T-cells from allogeneic (distinct genomes) bone marrow donors.

In some of these applications it is desired to separate cells on the basis of the presence (or absence) of more than one distinct cell surface marker. Such separations presently employ fluorescence activated cell sorting, on a cell by cell basis, and are used in clinical applications. Unfortunately, the current state of the art is limited to a few thousand cells per second rate, which requires about a day of instrument and operator time to sort enough cells (typical rescue doses are about $2 \times 10^6$ cells) that are about 1% abundant after a brief pre-purification using cell density dependent centrifugation.

Current magnetic bead techniques do not require the examination of each individual cell and thus require less sophisticated equipment and less operator attention as the separation is accomplished by simply placing the solution containing the magnetic bead-cell complexes in a magnetic field gradient for times of about an hour.

Prior Art Compared to the Present Invention

One limiting feature of prior magnetic bead techniques is that only one cell marker is targeted at a given time. The present invention uses magnetic particles with sufficiently distinctive character such that several such separations are performed in parallel or that fractions which are bound to particular combinations of markers can be isolated. The present invention achieves this goal by constructing particles whose magnetic moments are controlled both in magnitude and in magnetic field dependence using techniques developed for magnetic domain stabilization in sensors for magnetic storage applications. A key feature of the present invention is that multiple layers of ferromagnetic materials, whose properties are modified by the use of antiferromagnetic coupling or antiferromagnetic exchange bias, are used to tailor the magnetic response of particles for multiple separations or other applications. This feature is absent in prior art.

Basic Physical Considerations

Affinity bound magnetic beads in solution experience forces associated with magnetic fields, gravity, and collisions and electrical interactions with other solution components and container walls. Wall interactions are generally well understood and here the solution environment is considered only in terms of diffusion and viscous drag forces. Electrical forces in ionic aqueous media are generally of short range and, although useful in the context of colloidal stability and wall interactions, are well known in the art. The magnetic forces of interest in the present application arise from the applied magnetic field, and from the magnetic fields of the magnetic beads themselves. The latter forces are important because they can lead to the formation of aggregates of magnetic particles and their complexes.

A single separation is performed by applying a magnetic force that is not overwhelmed by gravitational forces. The application of such a magnetic force draws the magnetic beads into a region determined by the magnetic field so that non-magnetic components can be eliminated. If the bead-target complexes and the magnetic forces are all identical, and gravitation, diffusion and laminar flow issues are manageable, then the complexes all move at the same rate along a separatory column. However, in a single separation the goal is merely to collect all beads and complexes, and thus, there is no need for a column, homogenous beads or magnetic forces, and little concern regarding aggregation forces provided they are sufficiently weak to allow the beads to be suspended for mixing and binding or unbinding of their targets.

To perform a simultaneous separation of multiple targets, two magnetically distinct types of beads are employed by placing a mixture of the bound beads at one location in a generalized separatory column. In this case, the magnetic forces will be different for the different types of beads. If the bead-target complexes are all identical with respect to viscous forces and diffusion, then the two types of bead-target complexes move at different rates in the applied magnetic field and physically separate into two bands. It is clear that in the case of a multiple separation, aggregation of the distinct type of beads will destroy the perfection of the separation. Also, aggregation of beads of the same type may modify the magnetic and viscous drag forces on the aggregate and therefore alter the velocity of the affected complexes, resulting in a deviation from the ideal of separation into two bands.

The consequences of aggregation in the case of a multiple separation depend on the desired yield and purity of the separation. The yield and purity are limited by the loss of complexes from the desired bands and by the appearance of inappropriate complexes within the desired bands, respectively.

Finally, a separation can be performed wherein entities which carry multiple binding sites for each of two or more distinct markers simultaneously appear on a single target. The magnetic forces then depend on both the number and type of magnetic beads in the complex so that, even for identical viscous drag effects, multiple bands are expected. As a further complication, allow that the target-bead complexes can have significant variations in size and shape so that significant variations in viscous drag must be accommodated. Now the whole notion of separation into bands becomes questionable. This is the regime where separations resort to fluorescence activated cell sorting. This technique uses distinct fluorescently labeled beads, again conjugated to specific recognition molecules, so that the type and number of attached beads are distinguished on the basis of their optical fluorescence spectrum and intensity, respectively. This technique is not subject to strong complications resulting from variations in viscous drag coefficients, but does require that measurement and separation be made on a cell by cell basis.

The prospects for the extension of magnetic bead techniques to this realm would be markedly improved if beads with sufficiently distinctive magnetic characteristics and methods for overcoming possible problems associated with variations in viscous drag coefficients were made available. Consider first the distinctive magnetic characteristics aspect.

The magnetic force, F, on a magnetic bead due to an applied magnetic field is:

$$F = -\nabla(M \cdot H).$$

Here H is the external magnetic field and M(H) is the magnetic moment of the bead. For superparamagnetic beads, used in prior art in fields well below the saturation field (typically many thousands of Oersteds):

$$M(H) = \chi HV$$

where $\chi$ is the superparamagnetic susceptibility and V the particle volume. In principle distinct types of superparamagnetic beads could be made, for example, by altering $\chi$ through the magnetic loading or by altering V so that particles of different moments are formed. The net moment of an assembly of two types of such particles, containing $n_i$ particles of type i, is $M = n_1 M_1 + n_2 M_2$. In an ideal case where a column separation yielded discrete bands for each possible M, then $n_1$ and $n_2$ could be deduced for each band and indexed according to their content; i.e., fractions containing $M_1$ and $M_2$, $M_1$ not $M_2$, and $M_2$ not $M_1$. It is evident from the above that these particular fractions may occur within several bands because of variability in $n_i$, which is often not critical. If variations in viscous drag coefficients for the bound complexes or variations in the beads themselves cause deterioration of the desired bands, this method could fail because the velocity and location of a particular bound complex would then not provide sufficient information to determine the presence and/or absence of $M_1$ and/or $M_2$.

The present invention involves the fabrication of particles with distinct magnetic signatures so that the type of beads in a complex can be determined, independent of the value of $n_i$. These particles are layered structures wherein multiple ferromagnetic layers are constrained to have nearly zero net magnetic moment at zero magnetic field, to minimize aggregation problems. The magnetic moment dependence on the magnetic field is different for the distinctive particle types and is nonlinear for magnetic fields in the easily obtained range of tens to several hundreds of Oersteds. The distinctive effective susceptibilities allow an independent determination of the types of beads in the complex, much as distinctive spectral characteristics are exploited in the case of fluorescent beads. Furthermore, the nonlinear magnetic characteristics permit the use of separation schemes which facilitate the reduction of problems associated with viscous drag variability.

Forces Required for Separation

There are several physical issues and constraints that need to be examined before proceeding to understand the structures that are proposed. First consider colloidal stability, referring to the tendency of magnetic particles to settle out of solution. A rough estimate of stability can be made by comparing the gravitational potential energy difference for a particle over a cm height range with the thermal energy kT where $k = 1.38 \times 10^{-16}$ ergs/K is the Boltzmann constant and T is the temperature. For a sphere of radius r and density $\rho$ in a liquid of density $\rho_0$, the size is limited to:

$$r = 0.02 \text{ micron} \times (\delta\rho)^{-1/3}$$

where $\delta\rho = \rho - \rho_0$ is in gm/cm$^3$. For the materials used in the formation of the magnetic structures herein, $\delta\rho = 10$, settling will occur unless very small particles or low density coatings are employed. However, mild agitation is sufficient to overcome simple settling effects.

A more stringent criteria is that the magnetic forces be comparable to gravitational forces so that gravitational settling does not overwhelm magnetic separation. Equating the magnetic and gravitational forces on a particle gives:

$$MV\nabla H = \delta\rho V g,$$

where M is the magnetization, V is the particle volume, $\nabla H$ is the gradient of the magnetic field and $g = 1000$ cm/sec$^2$. For ferromagnetic materials M is about $10^3$ emu/cm$^3$ and $\rho = 10$ gm/cm$^3$, so that $\nabla H = 10$ Oersteds/cm. This magnetic field gradient is readily obtained. This calculation assumes the particles are comprised solely of ferromagnetic materials, but other materials can clearly be included within the beads if the field gradients are appropriately modified.

Particle Motion

The magnetic forces should also be sufficiently strong that the induced motion is not dwarfed by diffusion processes. The diffusion constant D is given by the Einstein-Smoluchowski equation:

$$D = kT/f$$

where f is the frictional drag coefficient.

For a small particle of radius r and small velocity v in an aqueous medium of viscosity $\eta = 10^{-2}$, the Reynolds number is small so that Stokes' equation applies and f is only weakly shape dependent. For an r=1 micron radius sphere $f = 6\pi\eta 2r = 4 \times 10^{-5}$; so D is about $10^{-9}$ cm/sec$^2$.

Since $\Delta x = (2Dt)^{1/2} = 0.6$ microns $(t^{1/2})$, diffusion is a slow process for such particles.

Stokes' equation also gives a particle translational velocity for a force F as v=F/f. The gravitational force on a 1 micron radius particle of $\rho = 10$ is $4 \times 10^{-8}$ dynes, so $v = 10^{-3}$ cm/sec. This velocity is reasonably small to allow time for separations.

Magnetic Aggregation at Zero Field

Concerns with aggregation of particles have already been expressed in several contexts. To understand the origin of these concerns, compare the attractive dipole—dipole interactions with those of thermal agitation. For single domain ferromagnetic particles with magnetizations of M=1000 emu/cm$^3$ and radius r, one equates the magnetic dipole-dipole interaction energy at contact, $M^2/(2r)^3$ ($M = 4/3\pi r^3 M$) with kT. This equality is satisfied for a particle of r=0.003 micron, which would require a truly ferromagnetic magnetic particle to be of extremely small dimensions. It is for this reason that most particles employed in present context are superparamagnetic. In superparamagnetism the magnetic alignment of the internal spins fluctuates due to thermal agitation, so that the net moment in zero applied field vanishes but monotonically increases to a saturation value at a saturation field which is typically many kiloOersteds. In the present invention, the magnetic moments of the individual ferromagnetic layers within a particle can be spatially oriented so that the net moment vanishes at zero field, but the saturation fields can be conveniently adjusted in the sub kiloOersted range.

Comparison of Superparamagnetism with Ferromagnetism

For superparamagnetic beads of prior art at fields below saturation, the magnetization $M = \chi H$ with $\chi = 10^{-2}$. The magnetic moment of a 5 micron diameter superparamagnetic bead is then roughly $M = 6 \times 10^{-13}$ H emu. For particles using this invention, the full saturation magnetization can be obtained at modest fields where the internal ferromagnetic layers become magnetically aligned. For a similar sized bead based on the present technology consider a 5 micron×5 micron×t (nanometer) permalloy film, where M is about $2 \times 10^{-11}$ t (emu), so that a 1 nanometer (nm) thick ferromagnetic film has a moment comparable to a 5 micron diameter superparamagnetic bead in a 100 Oe field. There is thus much freedom to add additional materials to manipulate the internal ferromagnetic thin films while maintaining magnetic moments and dimensions comparable to those of prior art. Such added materials could also include polymer encapsulants and materials to aid in noncovalent or covalent attachment of biological recognition molecules. An overview of suitable methods for the attachment of biological recognition molecules is given below. The particle dimensions can also be adjusted to improve performance or reduce costs. For 5 micron particles, the number of particles available from a 1 cm$^2$ film is roughly $4 \times 10^6$/cm$^2$ which is comparable to the stem cell "rescue dose" for one human.

Properties and Preparation of Magnetic Particles

The following section describes the properties and preparation techniques used in the present invention for the magnetic particle of the present invention.

Particle Manufacturing and Overcoming Aggregation

The methods used in the fabrication of certain types of magnetic heads can be directly adapted to allow the use of strongly ferromagnetic materials in structures which have no net dipole moment in zero field. These methods rely on materials and structures which produce ferromagnetic layers which align in an antiparallel fashion in zero field through the use of antiferromagnetic exchange or magnetostatic coupling of magnetic layers separated by non-magnetic spacers, or on ferromagnetic layers which are "pinned" in different directions by exchange coupling to antiferromagnetic layers. An example of the latter type of structure and coupling mechanism are implicit in the spin valve. Here, one has a ferromagnetic layer which is pinned along a pinning axis by exchange coupling to an antiferromagnetic layer.

Figure 1:
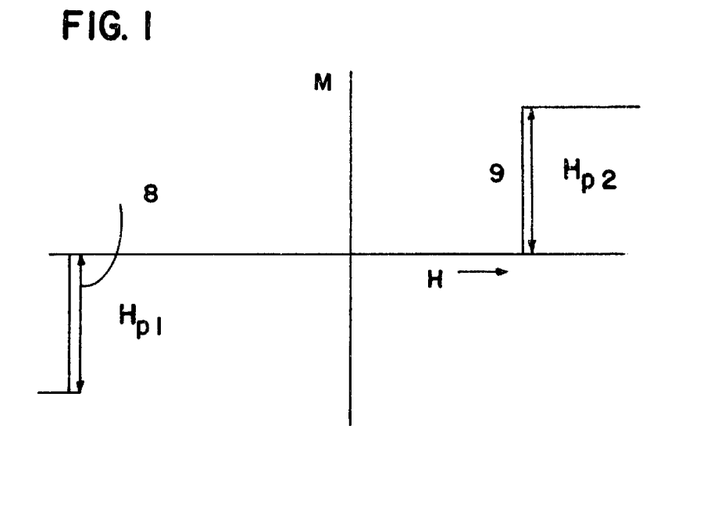
FIG. 1 shows the behavior of the magnetic moment of a typical structure of the present invention in the presence of a magnetic field applied along the magnetic pinning axis, also referred to as the easy axis.

There is also a "free" ferromagnetic layer which is magnetically isolated from the pinned layer by a nonmagnetic spacer. Each ferromagnetic layer has a magnetic moment which displays a hysteretic M(H) loop as the field is varied. The free layer loop is centered at low fields while the pinned layer loop center can be offset to field values ranging up to thousands of Oersteds through the use of exchange bias. Since the magnetic moments of the two layers "flip" at different fields, the moments of the layers can be aligned along different directions, depending on the value of the applied field. For the present invention, it is desirable to limit magnetic aggregation by assuring that the net moment be small in zero field. To achieve this goal, two layers of equal moment can be pinned in opposite directions so that there is an adjustable range where magnetic fields along the easy axis leave the moments antiparallel. FIG. 1 shows the magnetic moment as a function of an external field applied along the pinning axis for a pair of ferromagnetic films with equal magnetic moment and opposite pinning fields $H_{p1}$ 8 and $H_{p2}$ 9. Fields between these values produce no net moment, but fields outside of this range induce the pinned layers to take on parallel alignment. Other forms of magnetic coupling which similarly control the relative alignment of layered magnetic films can be similarly exploited.

Figure 2:
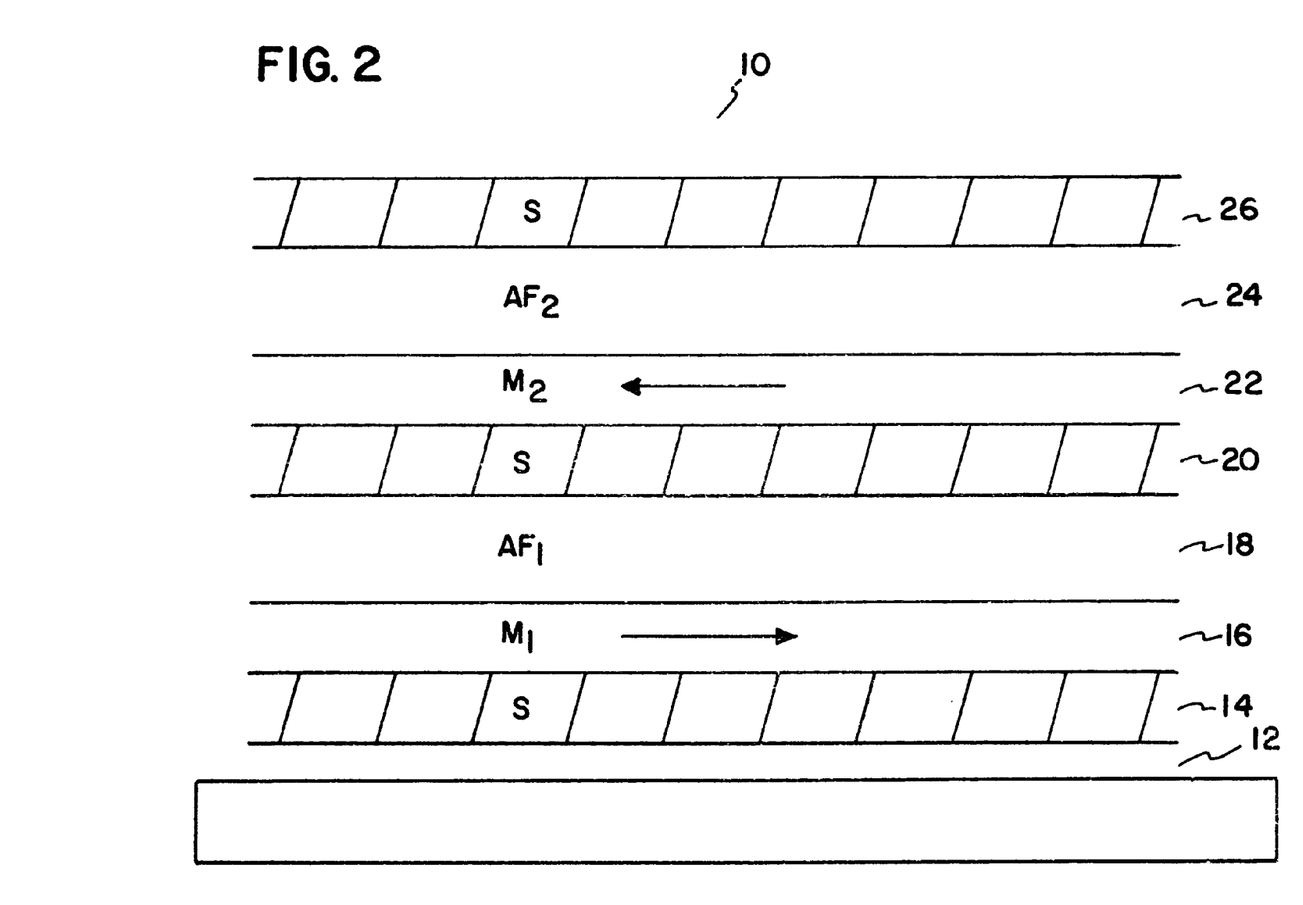
FIG. 2 shows a typical layer structure used for making the magnetic particles of the present invention.

FIG. 2 shows a typical layer structure 10 used for making the magnetic particles of the present invention. A substrate with a lift off layer 12 is used as the base for growing or sputtering additional layers onto the overall structure 10. Spacer layer 14 is applied to lift off layer 12, either via sputtering, vacuum deposition, or other attachment process. The spacer layer 14 may or may not be necessary to establish the proper magnetic properties or to aid in the binding of a coating to the structure. A first magnetic layer 16 is then coupled to the spacer layer 14. The thickness of magnetic layer 16 depends on the dipole moment and pinning field desired, on the materials being deposited, and the overall moment of the structure 10. Typical magnetic layer 16 thicknesses are between 1 and 50 nanometers.

A first antiferromagnetic layer 18 may then coupled to first magnetic layer 16. The antiferromagnetic layer 18 biases the dipole moment of magnetic layer 16 to prefer orientation along a given direction, called pinning the dipole moment of magnetic layer 16. Typical antiferromagnetic layer 18 thicknesses are between 0 and 50 nanometers. Typical antiferromagnets used for exchange biasing include certain oxides of iron and nickel and several manganese alloys such as FeMn, NiMn, IrMn, PtMn, etc.

A spacer layer 20 may then be attached to antiferromagnetic layer 18. The spacer layer 20 provides separation between the antiferromagnetic layer 18 and further layers of magnetic material, and may be of value for helping to define the magnetic characteristics of subsequent layers within the structure 10. This spacer layer may be unnecessary. For example, if spontaneous antiferromagnetic coupling is used, then the antiferromagnetic layer 18 may be omitted and the spacer layer 20 thickness and composition adjusted to obtain the desired antiferromagnetic coupling.

The structure 10 then has a second magnetic layer 22 coupled to spacer layer 20 to allow control of the net magnetic moment of the ferromagnetic layers which comprise the structures 10. To alleviate the problem of aggregation, the orientation of the dipole moment of second magnetic layer 22 is typically substantially opposite to that of first magnetic layer 16, but can be at other angles, including parallel to the dipole moment of first magnetic layer 16, depending on the strength of the dipole moment and overall characteristics desired for the structure 10.

A second antiferromagnetic layer 24 may then be coupled to second magnetic layer 22. The second antiferromagnetic layer 24 keeps the dipole moment of magnetic layer 22 oriented in a given direction, called pinning the dipole moment of magnetic layer 22. This second antiferromagnetic layer may be unnecessary if spontaneous antiferromagnetic coupling is obtained through control of spacer layer 20 or from demagnetization fields.

A spacer layer 26 is then attached to second antiferromagnetic layer 24. The spacer layer 26 may or may not be necessary to protect the ferromagnetic and antiferromagnetic layers and may aid in the binding of a coating to the structure.

The relative pinning directions of the ferromagnetic layers 16 and 22 can be different and can be set by several methods. For some antiferromagnetic exchange bias materials, the ferromagnetic layers can be set in opposite orientations during manufacture of the structure 10 by reversing an applied magnetic bias field when the second magnetic layer 22 is grown. The layers can also be set antiparallel after the structure has been grown by using antiferromagnets with different elevated blocking temperatures for layers 18 and 24. In this case the pinning of each ferromagnetic layer is set by the field which is present when the sample is cooled through the blocking temperature of its biasing antiferromagnet.

The structure 10 shown in FIG. 2 is shown for illustration only and is not meant to limit the scope of the invention. Other structures, using more or less spacer layers, more or less magnetic layers with varying magnetic strength, varying directions of dipole moments, and varying numbers of antiferromagnetic layers are possible within the scope of the present invention.

Fabrication of structures 10 are straightforward using sputtering, vacuum deposition, growth, vapor deposition, and epitaxial growth procedures. The structure 10 can be grown as a film and then separated into particles using a number of techniques, including using photoresist and subtractive etch methods with a suitable underlayer or lift off layer 12 to allow their release from the substrate. Alternatively, a suitably injection molded or photoresist fabricated patterned template and a release agent could allow simple lift off from a reusable template. Deposition onto performed particles is still another alternative.

The value of the pinning fields can be easily estimated. As an example, for an 80:20 NiFe layer (shown as layers 16 and 22 in FIG. 1) of 5 nanometer thickness pinned by 50:50 MnFe of 10 nanometer thickness (shown as layers 18 and 24 in FIG. 1), the value of $H_p$ (in Ta/NiFe/MnFe/Ta layer structures) is about 300 Oe and scales as the inverse of the magnetic layer thickness. Hence the same moment can be obtained by using two exchange biased 2.5 nanometer NiFe films but the pinning field for each would increase to about 600 Oe. It is well known that the magnetic moments of films may not be linear in the film thickness for films in this thickness range but adjustments in the physical thickness to compensate for such deviations are straightforward. Similarly, it is well known that the value of the exchange coupling depends upon the structure of the deposited material but this can be determined and controlled empirically. By laminating different numbers of such layers (16 and 22) with different ferromagnetic layer 16 and 22 thicknesses both the saturation moments and fields where the ferromagnetic saturation occurs can be varied. If several groups of distinct particles are made and each group of structures is conjugated to distinct biological recognition molecules, the present invention has the ability to sort the different biological marker bearers by using the field dependence of the mobility of each magnetic particle group.

Calculation of Energy of a Particle in an Applied Field

The idealized magnetic behavior shown in FIG. 1 appears to offer particles whose magnetic moment abruptly switches on when the applied field increases through the pinning field. The simple discussion above is qualitatively correct for the case where the applied field is along the pinning axis. However, if the particles are free in solution they can easily rotate their pinning axes away from the applied field direction in order to attain the minimum energy orientation. This rotation arises because of the torque, M×H. For a small particle of radius r, this torque corresponds to a rotational force $F_{eff}$=MH/r which is large compared to the forces due to typical magnetic field gradients. If H/X represents the magnetic field gradient, then $F_{eff}$ is enhanced over the gradient induced forces by the ratio X/r which is 1000 for x=1 mm and r=1 micron. A similar argument applies if a particle is initially aligned with the thin magnetic film dimension perpendicular to the applied magnetic field direction, but now with r replaced by t in the nanometer range. Hence, very strong torques operate to align particles so that the applied filed is in the plane of the ferromagnetic films. Thus the orientation of the particles is strongly determined by the requirement for zero torque which occurs at the minimum energy configuration. The energy of two magnetically decoupled, magnetically soft, and oppositely pinned moments M1,2 in an applied field $H_a$ oriented at an angle θ with respect to the pinning axis can be modeled as:

$$E=-M\{(H_{p1}^2+H_a^2+2H_{p1}H_a \cos θ)^{1/2}+(H_{p2}^2+H_a^2-2H_{p2}H_a \cos θ)^{1/2}\}$$

Figure 3:
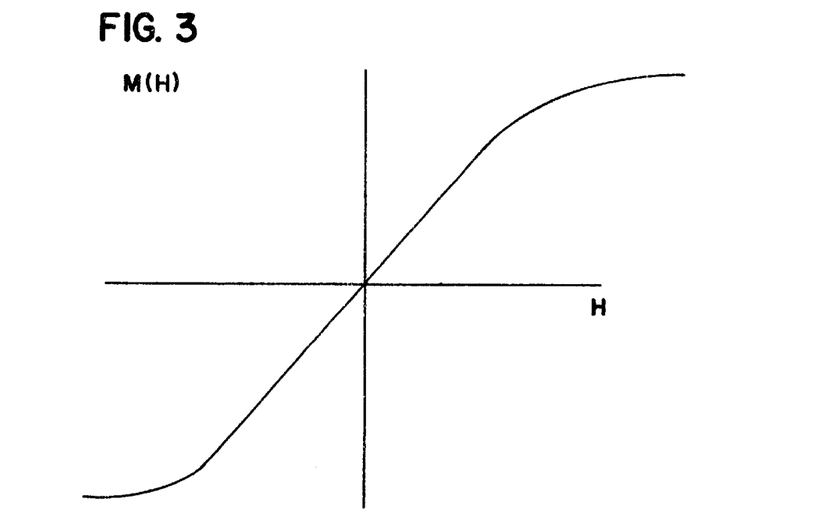
FIG. 3 shows the magnetization curve for the case of right angle alignment between the applied field and the particle pinning axis for the present invention.

The correct branch of the square root has been chosen for $H_a<H_{p1,2}$ with $H_{p1,2}$ the pinning fields. When $H_{p1}=H_{p2}$, dE/dθ when sin(θ)cos(θ)=0. At sin(θ)=0, the particles align with their pinning axes along the applied field and the increase in the energy for one moment exactly compensates the decrease for the other. The total energy is independent of the applied field at this point of maximum energy. When cos(θ)=0, the pinning axis is perpendicular to the applied field. In this case, both moments rotate as the field is applied to have a component along the applied field of $Ha/(H_a^2+H_p^2)^{1/2}$. The net magnetization increases, initially linearly, and goes smoothly from 0 to 2M, gradually saturating at fields $H_a>H_p$. The abrupt transition from antiparallel to parallel alignment at Hp is clearly lost. The particle itself can maintain the same rotational orientation with its pinning axis perpendicular to the field as the field is increased because the net moment produces no torque. FIG. 3 shows the magnetization curve for the case of right angle alignment of the fields of the particle of the present invention.

In a more general case where $H_{p1}>H_{p2}$, it is easy to show that as the field is increased the net moment first arises at right angles to the pinning direction but, as $M_1$ is less susceptible to rotation, the particle gradually rotates to align at an angle where the moment is between the pinning axis and its perpendicular. It is easy to show that in this case: cos(θ)=$(H_a/2)(1/H_{p2}-1/H_{p1})$ for $H_a<H_{p1}$, $H_{p2}$. In the extreme case where $H_{p1}>>H_{p2}$, this expression shows that the particle rotates from the right angle orientation, preferred at low fields, to align the net moment along the pinning axis at large applied fields. Thus the saturation magnetic moment is obtained more rapidly with increasing field than in the case where $H_{p1}=H_{p2}$. The above model is not intended to be fully quantitative, as it neglects coercivities, anistropies, demagnetizing fields, etc.

Qualitatively similar behavior can be expected if other forms of antiferromagnetic coupling are employed. These might include antiferromagnetic or biquadratic coupling through nonmagnetic spacers or antiferromagnetic magnetostatic coupling associated with "magnetic charges" on the surfaces of patterned structures.

Constraints on Particle Manufacturing

The thickness and lamination of the magnetic layers is subject to some constraints because the self generated magnetic fields of the particles affect both the behavior of the magnetization and particle aggregation. These fields result from equivalent magnetic "surface charges" which occur at edges where the magnetization is normal to a surface. Demagnetization fields from a film act on the film itself to cause anisotropies and act between adjacent films to tend to align the layers in an antiparallel sense. These demagnetization fields also provide a rough estimate of the fields when 2 particles aggregate in a head to tail chain, or a side by side, antiparallel sense.

In the specific case of antiferromagnetic exchange bias, these fields can be held to small values so that they can be neglected as compared to pinning fields and the applied fields used to control the particles. The demagnetizing field can be estimated from the induced "magnetic surface charges" at the ends of a film. For length l, width w and thickness t, the line charge density along the width is Mlt. The field at the center is then roughly Mwt/l². A better estimate for a ferromagnetic NiFe film with t<w<l and M directed along w is:

$$Hd=π^2M×(t/l)=10×t(nm)/l(um)Oe.$$

The aspect ratio t/l can be constrained to keep Hd below some tens of Oersteds which can further be kept small compared to Hp. Other shapes, such as discs, can also be used to alter the anistropy and the magnitude and spatial structure of demagnetization fields.

It is important to realize that particles containing laminated ferromagnetic layers with antiparallel moments do produce external magnetic fields. For parallel moment alignment the net moment is 2Mwtl which acts as a dipole source from which external fields can be readily estimated. The external fields are much weaker in the antiparallel orientation because there is no net moment. In this state, the "magnetic charges" at a given end of two antiparallel layers will have opposite signs. For antiparallel layers spaced by s, there are thus oppositely directed dipoles at each end of the particle. These dipoles have moments which are roughly Mwts=10–15 wts with w in microns and t and s in nm, which are reduced in magnitude, relative to parallel alignment, by a large value of l/s=$10^3$. External fields at large distances further become quadrupolar in nature as the end dipoles are oppositely oriented.

The possibilities of spontaneous aggregation of the particles must also be addressed. One criterion is the ratio of the attractive interaction energy and the thermal energy kT. For a single magnetic layer of dimensions 5 micron×5 micron×5 nm and magnetization of 1000 emu, the field H where MH=kT is H=$4\times10^{-4}$ Oe. Given that demagnetizing fields were estimated as below tens of Oersteds, aggregation is expected for particles whose ferromagnetic layers are aligned by a magnetic field. In the antiparallel orientation the external fields are reduced by three orders of magnitude and thermal energies are not so different from interparticle interaction energies. Further reductions in external fields in the antiparallel state can be obtained by stacking multiple magnetic layers to eliminate dipoles for quadrupoles, etc. However, we find that aggregation in the demagnetized state is not a problem as particles which have gravitationally settled into dense assemblies are easily resuspended as isolated particles by mild agitation in low field.

Aggregation problems are important in the parallel aligned state because the particles may ultimately clump together magnetically, possibly linking distinct species which one may desire to separate. Assume that all phases of particle-recognition molecule attachment and complex formation with targeted entities are performed and nonaggregated complexes are placed in a separatory apparatus and the magnetic field is subsequently turned on. To estimate the time that elapses before interparticle magnetic forces draw the particles together, consider the solution velocity as given by Stokes' equation for an aqueous solution using dipolar interparticle magnetic forces for two particles with magnetic moment M. Very roughly one finds:

$$6\pi\eta a\, dR/dt = M^2/R^4,$$

where a is the particle diameter and R the separation. A time to contact can be estimated by integration to be t=$\pi\eta a R_0^5/M^2$, where $R_0$ is the initial separation. For a 5 micron×5 micron×5 nm NiFe film at saturation, M is about $10^{-10}$ (emu). For t=$10^4$ sec, $R_0$ falls in the micron range so that if $R_0$ is held at 100 microns aggregation should not be problematic on the time scale of hours. This corresponds to particles which are suspended at reasonable densities of about $10^6/cm^3$. Actual densities can be further decreased to allow for statistical variations. This treatment assumes that the particles are interacting through a simple attractive $R^{-4}$ force law. For magnetic dipoles the actual forces are much more complex as they are attractive for some relative orientations and positions of the dipoles and repulsive for others. It is well known that dipoles can coalesce to form chains wherein particles with parallel dipoles link together along their mutual dipolar axis via attractive forces between their respective north and south poles. If, however, parallel particles positioned in a head to tail chain configuration are rotated by 90 degrees, by rotating the external field, prior to coalescence then the forces become repulsive as like poles become proximal. Thus magnetic field rotations and or temporal reorientations may be useful for limiting aggregation phenomena.

Fabrication of Particles for Evaluation

Figure 4A:
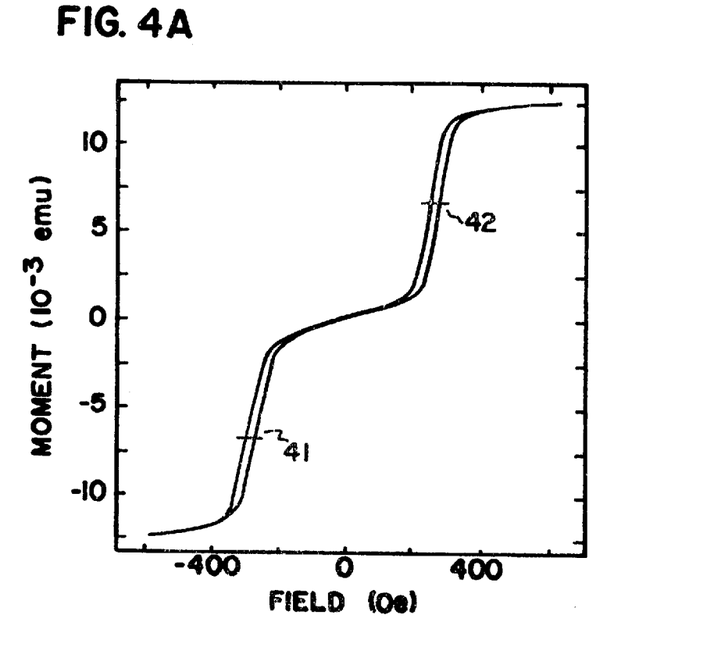
FIGS. 4A–4D show magnetization curves for distinct particle types with the magnetic field parallel and perpendicular to their pinning axes.
Figure 4B:
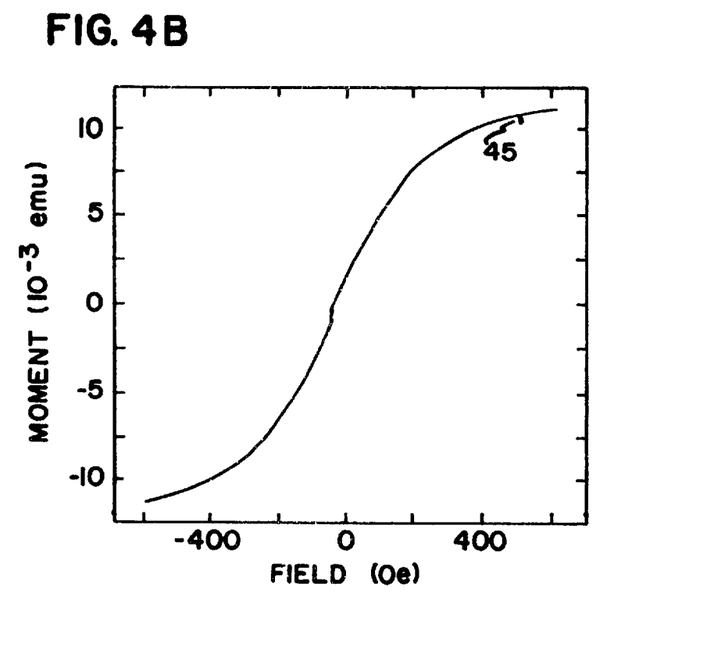

Test structures have been fabricated using ion beam sputtering as the deposition source. First, Si wafers were cleaned and precoated with a 5 nm tantalum (Ta) film to promote adhesion of an organic lift-off layer. This layer was cast by spin coating a 1.4 micron film of precured polyimide in anisole, followed by a 30 minute bake at 110 C. Metallization was then applied to make several different examples of magnetic structures. One sample, denoted S1, had a structure:

substrate/5Ta/5Py/9FeMn/3Ta/5Py/9FeMn/3Ta/5Py/9FeMn/*revH*/ 3Ta/5Py/9FeMn/3Ta/5Py/9FeMn/3Ta/5Py/9FeMn/5Ta Here the thickness of a material is given in nanometers followed by the elemental composition. Py refers to permalloy of about 80:20 Ni:Fe composition which comprised the ferromagnetic material. FeMn is of about 50:50 composition and was used as the pinning antiferromagnet. Ta spacers were used to separate magnetic materials, to set up crystalline texture advantageous for exchange bias, and as a protective cap. The notation *revH* refers to the fact that a magnetic field of some tens of Oersteds was applied to set the pinning direction throughout growth and was reversed in direction after the first set of magnetic layers was completed. The magnetization loops of this sample were recorded using vibrating sample magnetometry with the field parallel and perpendicular to the pinning axis are shown in FIGS. 4(A) and (B), respectively. A second structure, denoted S3, was grown with the following structure:

substrate/3Ta/20Cu/5Ta/15Py/9FeMn/*revH*/3Ta/15Py/9FeMn/ 3Ta/20Cu/5Ta.

Figure 4C:
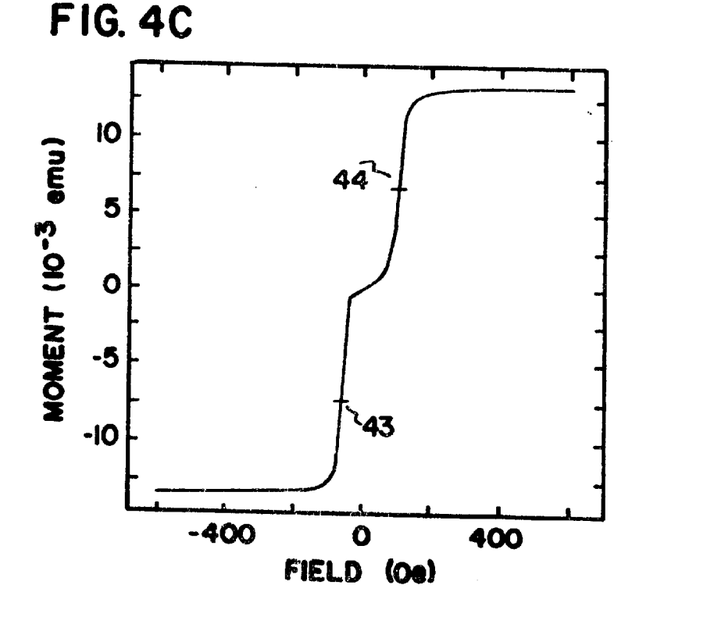
Figure 4D:
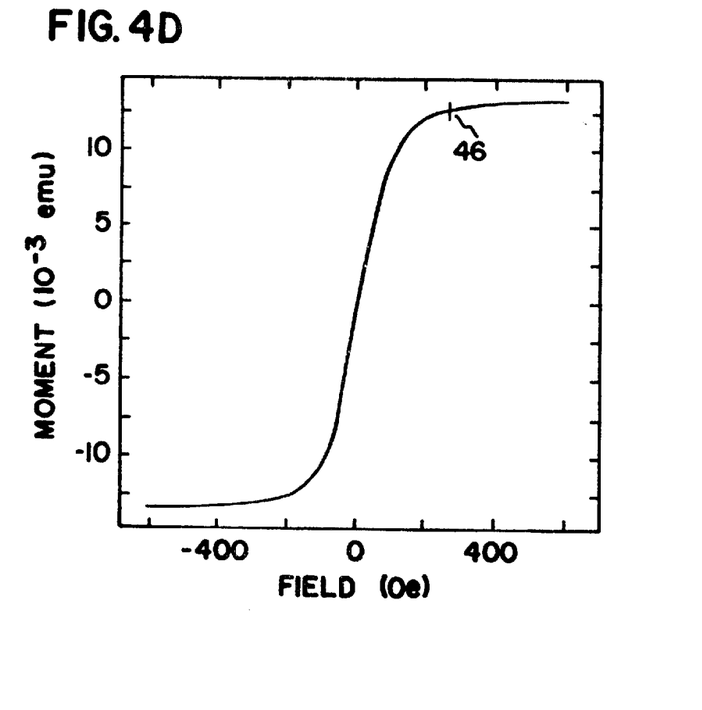

The total Py thickness is same for S3 as for S1, but the FeMn exchange coupling is expected to be weaker for S3 because of the thicker individual Py layers. The Cu layers in S3 were used to maintain roughly the same thickness as S1 but to also provide a distinct color. FIGS. 4(C) and (D) show the corresponding magnetic behavior for S3. The attainment of different pinning, 41–44, and saturation, 45 and 46, fields and of low magnetization in zero field are clearly evident. There are small deviations in the values of the predicted pinning fields and in the magnetic moments but these can be easily corrected by empirical modification of film thicknesses.

The wafers were then spin coated with a 1.3 micron chemically amplified polyimide resist and baked at 95 C for 5 min. They were next placed in contact with a 5 micron checkerboard mask, 1 $cm^2$ in area, and exposed for about 1 sec to 50 millijoules of UV radiation. A post exposure bake at 95 C for 2 min was performed and the pattern was developed using immersion in an alkaline developer for about 30 sec. The photoresist pattern was transferred into the metallization by using ion milling to remove the metal layer in regions not covered by the developed photoresist pattern. The lift off underlayer was dissolved in warm n-methyl pyrrilidinone using agitation and the bare substrate was removed from the solvent. The particle bearing solvent was transferred to test tubes and a small, 500 Oe, magnet was used to collect the magnetic particles so that the organic solvent could be extracted and exchanged for water. The distinctive particles were ultimately placed in different tubes, each containing about 1 cc of water, at an estimated density of $4 \times 10^6/cm^3$.

Separation of Particles in Solution

Figure 5A:
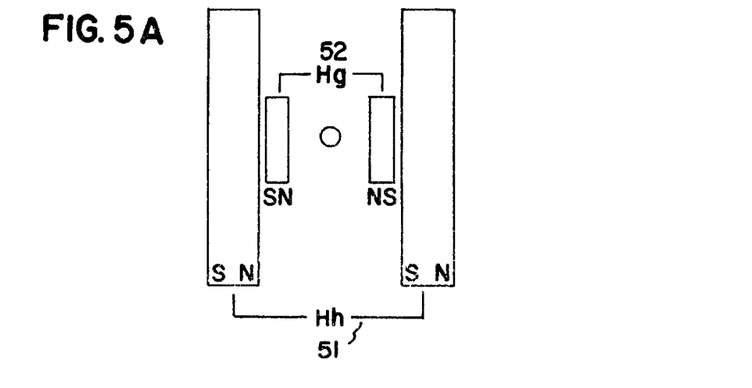
FIGS. 5A–5C illustrate one possible embodiment for separating the magnetic particles of the present invention using time dependent magnetic fields.
Figure 5B:
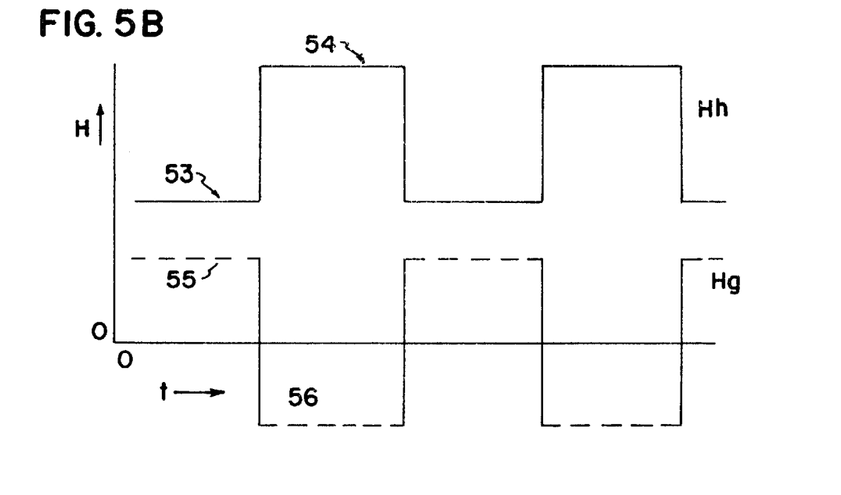

With this insight into the magnetic properties of the desired structure disclosed in the present specification, it is appropriate to discuss one mechanism of physical separation which is unique to such particles. For the present discussion, we consider the magnetic field to be comprised of two different horizontal components which are illustrated in FIG. 5(A). The first field is a relatively spatially homogenous field Hh, 51, which can be pulsed in time. The second field Hg, 52, has a relatively large gradient but a small value in the region of interest and can also be temporally pulsed. For the purpose of illustration, consider that the particles fall vertically in solution under the influence of gravity in the absence of magnetic fields. The homogenous field, Hh, is used to induce a magnetic moment in the suspended particles while the gradient field, Hg, is used to induce motion of the magnetized particles. If the gradient field is symmetrically pulsed in alternating opposite directions while Hh is held constant, then the lateral direction of motion of the magnetic particles will also alternate so that no net lateral displacement will be induced by the magnetic fields. If, however, Hh is varied between two different values, 53 and 54, synchronously with the alternation of Hg, 55 and 56, as shown in FIG. 5(B), then net lateral displacement will result if the magnetic moment depends on the value of Hh. Thus if Hh is held above the saturation field of one type of particle then no net lateral displacement will accrue for this type of particle. If Hh is held well below the saturation field for a second type of particle, whose moment is therefore roughly linear in Hh, lateral displacement will accrue.

Figure 5C:
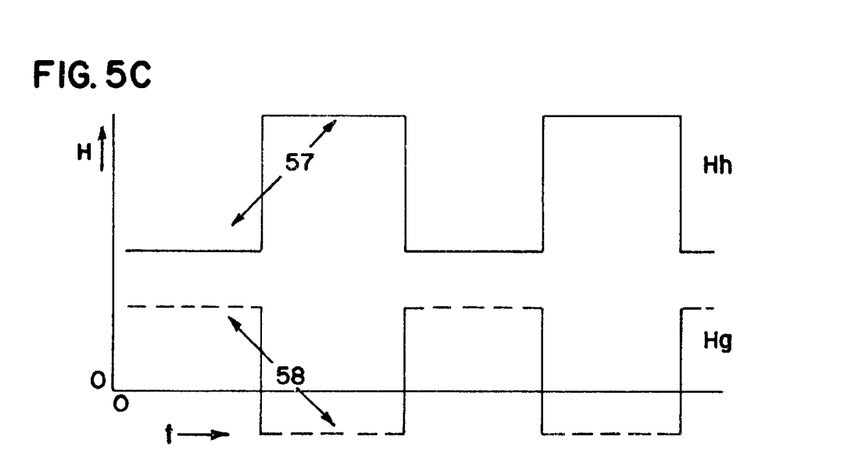

If the structure of the pulses is made asymmetric then alternative separation schemes can easily be achieved. Suppose that Hh is switched varied between H1 and 2H1, 57, while Hg is synchronously switched between H2 and –H2/2, 58, as depicted in FIG. 5(C). Now particles whose moment is linear in Hh will not accrue lateral displacements as contrasted with particles which remain saturated. Indeed the latter particles will move only half as fast laterally and thus half as far horizontally during the reverse field cycle so that substantial horizontal displacements can accrue. It is clear that similar manipulations are possible if the pulsewidths for different signs of Hg, or variations in the sign of Hh are allowed. It is further evident that these separation schemes do not require precise linearity or total saturation as adjustments in various parameters can be made to compensate for the actual magnetic characteristics. Finally, it is also straightforward to reorient the field directions relative to gravity or to include other forces in these separation schemes to achieve systems where, for example, some species are allowed to settle while others are levitated.

Figure 6:
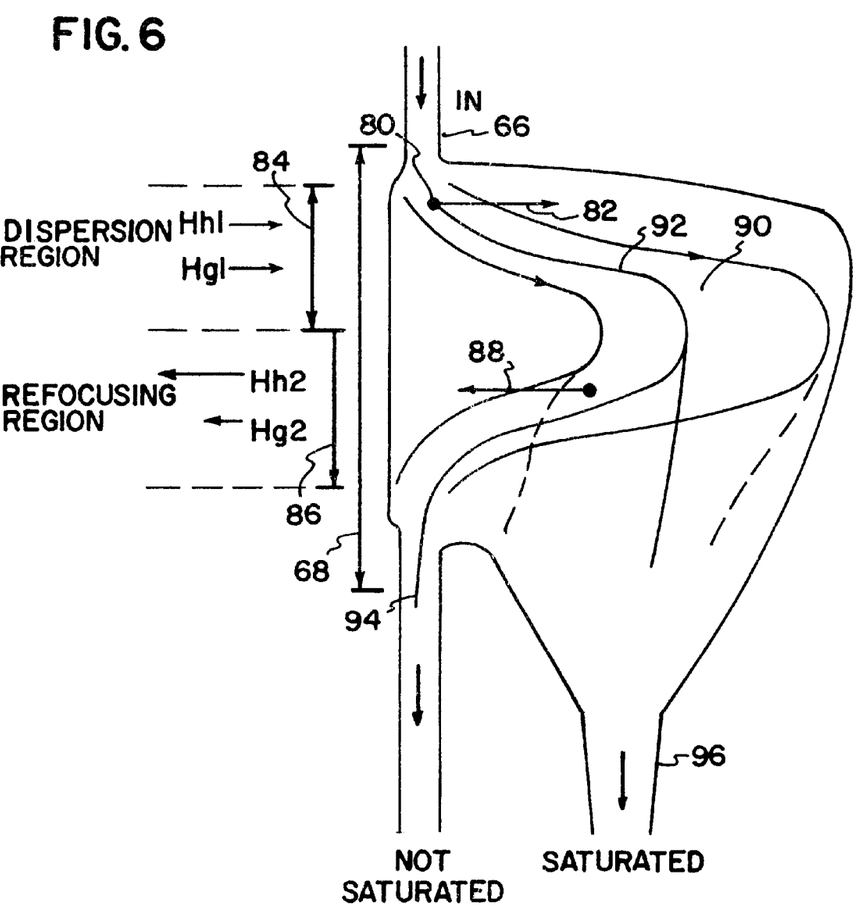
FIG. 6 illustrates an alternative embodiment employing spatial dependence and static fields to separate particles of the present invention.

FIG. 6 illustrates one possible embodiment for separating the magnetic particles of the present invention using spatially separated static fields.

Inlet 66 allows a given solution, possibly magnetic bead complexes with human blood, to enter into a region 68 that is exposed to magnetic field influences. For illustrative purposes only, the magnetic field is separated into homogenous and gradient components, Hh and Hg, and a single particle 80 is shown initially in region 68.

The magnetic moment of a given magnetic particle 80 will induce a velocity of magnetic particle 80 in direction 82 in a dispersion region 84. Similarly, refocusing region 86 will deflect particle 80 in direction 88 within refocusing region 86. Particles of various moments can be deflected different lateral distances away from the vertical trajectories associated with gravitational settling from inlet 66.

As particle 80 moves through dispersion region 84, particle 80 experiences a horizontal field Hh1 and a gradient field Hg1. Dispersion region 84 deflects particle 80 in direction 82 proportional to the strength of the magnetic moment of particle 80 and the strength of the magnetic field Hg that is applied. The vertical force is constant, and the trajectory 90 of particle 80 may have a curvature 92 associated with non-uniformities in the overall magnetic field. If variations in cell size, density, viscous drag forces, and number of particles 80 bound are present the trajectories 90 for different particles 80 will disperse.

In refocusing region 86, the magnetic field Hh2 or the gradient field Hg2 are reversed. The trajectory 90 can refocus particle 80, for example if Hh1=Hh2 and Hg1=–Hg2, because diffusion and interparticle interactions are negligible. This refocusing action will not work properly if the homogeneous magnetic field is different in the dispersing and focusing regions and the beads are designed to have a non-linear dependence of M on Hh.

For example, if Hh2=2 Hh1 and Hg2=–½ Hg1, refocusing will occur provided the magnetic moment of particle 80 is linear in H below the value 2Hh1. If this is the case, particle 80 will enter outlet 94, because the field has drawn particle 80 in direction 88 the same amount that particle 80 was dispersed in direction 82.

If M is nearly saturated at Hh1 then the refocusing deflection in direction 88 is only half of the dispersing deflection in direction 82. Thus, the saturated particles 80, which are now "focused cells," can be collected as those with saturation at fields below 2Hh1 in outlet 96. The particles from outlet 94, which did not saturate for fields below 2Hh1 can be further tested for saturation at higher fields by using the outlet 94 as an inlet to another set of fields similar to the ones described above, with different values for the field strengths. Alternative schemes are obviously possible. For example, one could choose Hh2=Hh½ and Hg2=–Hg1 to collect particles which are saturated at field values above Hh½ at outlet 94.

It is straightforward to devise schemes wherein separations for given types of markers can be obtained by connecting different sorters as serial logical elements to discriminate for or against single bead types or combinations of bead types. For example, consider a case where the presence of markers M1 and M2 are desired, while M3 is to be selected against. Presume distinct beads are available which saturate at 50, 150, and 450 Oe. First, nonmagnetic species can be trivially eliminated. To eliminate M3 containing complexes, the M3 bead can be chosen to be the 450 Oe bead and one can use Hh1=900 and Hh2=450 and Hg2=–Hg1 to reject any complex containing M3 but to refocus complexes containing M1 and/or M2 into outlet 94. To require M2, choose M2 to correspond to the 150 Oe bead, use Hh1=50 and Hh2=100 with Hg2=Hg½. Now complexes containing only M2 will refocus at outlet 94 of the second sorter and can be discarded. Beads containing only M1 or M1 and M2 can be collected at outlet 96 and further separated by using Hh1 =25 and Hh2=50 with Hg2=Hg½. Refocused beads at outlet 94 of this stage contain only M1 so that the desired M1 and M2 fraction appears at outlet 96 of this stage. The refocusing action exploited here for positive or negative selection is explicitly mentioned because the fractions which appear at outlets 94 are deliberately intended to return to their initial lateral positions independent of variations in the value of viscous drag coefficients.

This distinct separation of particles cannot be obtained at convenient magnetic fields with the superparamagnetic beads currently used because the currently used particles have very high saturation fields. Composites of small, randomly oriented or demagnetized ferromagnetic particles would suffer similar problems and others related to poor control of particle shapes, saturation fields, coercivities, or irreversible magnetization.

Observations of Test Particles in Applied Magnetic Fields

The particles were easily detected, but not resolved, by the unaided eye using specularly reflected light. Noticeable settling occurred over tens of minutes but the particles were easily dispersed by shaking. The motion of the particles in the field of a 1 in diameter, ½ in thick Alnico magnet contacting the outside wall of the tube was easily observed and the velocity was of the order of 1 cm/sec. A noticeable enhancement in reflectivity of the dispersed particles was noticed. If a weak magnetic field, measured as 1 Oe, was applied in a direction where field induced alignment of the particles with the magnetic field in the plane of the laminated films, then an enhancement in specular reflection was observed depending on the location of the light source and observer. As previously mentioned, very weak fields are sufficient to orient the particles so that the applied field is in the plane of the magnetic films. Optical microscopes were used to observe the particles using both reflected and transmitted light. Some observations were carried out in applied magnetic fields in an apparatus which used two water cooled electromagnets driven by pulsable current sources, much as illustrated by FIG. 5(A). The first electromagnet had 2 6" diameter coils with a 4" spacing which were connected in a configuration where the fields added to give a relatively homogeneous field of about 50 Oe/Ampere. The second electromagnet was comprised of 2 2" diameter coils at a 2" spacing which were connected in an antiparallel sense so as to obtain zero net field at their center but a field gradient of about 40 Oe/cm-Amp. Qualitative optical observations confirmed that the particle velocities showed the expected distinctive saturation characteristics as a function of the homogenous field and the expected linear variations in the gradient field amplitude. Various pulse schemes were examined to confirm the reversal of particle motion with the reversal of the field gradient or with the reversal of the homogenous field. These observations qualitatively verified that the particles behaved as expected.

Formation of chain-like aggregates was also noticeable if the settled beads were shaken once or twice by hand and then subjected to strong fields for tens of minutes at the relatively high concentrations given above. These chains allowed an easy visualization of chain rotation expected during reversals of the homogenous field and of the expected variations in the sign of inter-chain forces as a function of the relative position and orientation of proximal chains. Also, the interactions of the beads and chains with the container walls suggested some straightforward methods for using the walls to advantage during separations. For example, it was simple to adjust the magnetic field and gradient so that the trajectories of certain types of beads introduced at the top of a filled container intercepted the walls if the container which was deliberately canted relative to the vertical trajectories due to gravitation. The intercepting species dramatically slowed or stopped at contact while other beads could continuously move downward parallel to the canted wall. In a pulse mode where lateral motion periodically reversed, this led to a situation in which the wall intercepting beads were free to move during the reverse motion portion of the cycle so that they were systematically delayed in their downward motion. Field rotations were also found to be effective in inducing a type of motion which might be described as "walking". Here a bead in contact with the surface in a flat orientation for a field parallel to the wall turns upright when the field is rotated 90 deg and returns to a flat orientation when the field is at 180 deg. The beads center moved by the bead lateral dimension during the process because the bead end in contact with the surface remained stationary. There was some variability in the wall interactions between particles and/or regions of the walls in our observations of wall related phenomena but no efforts were made here to treat or clean the as received container walls.

Figure 7:
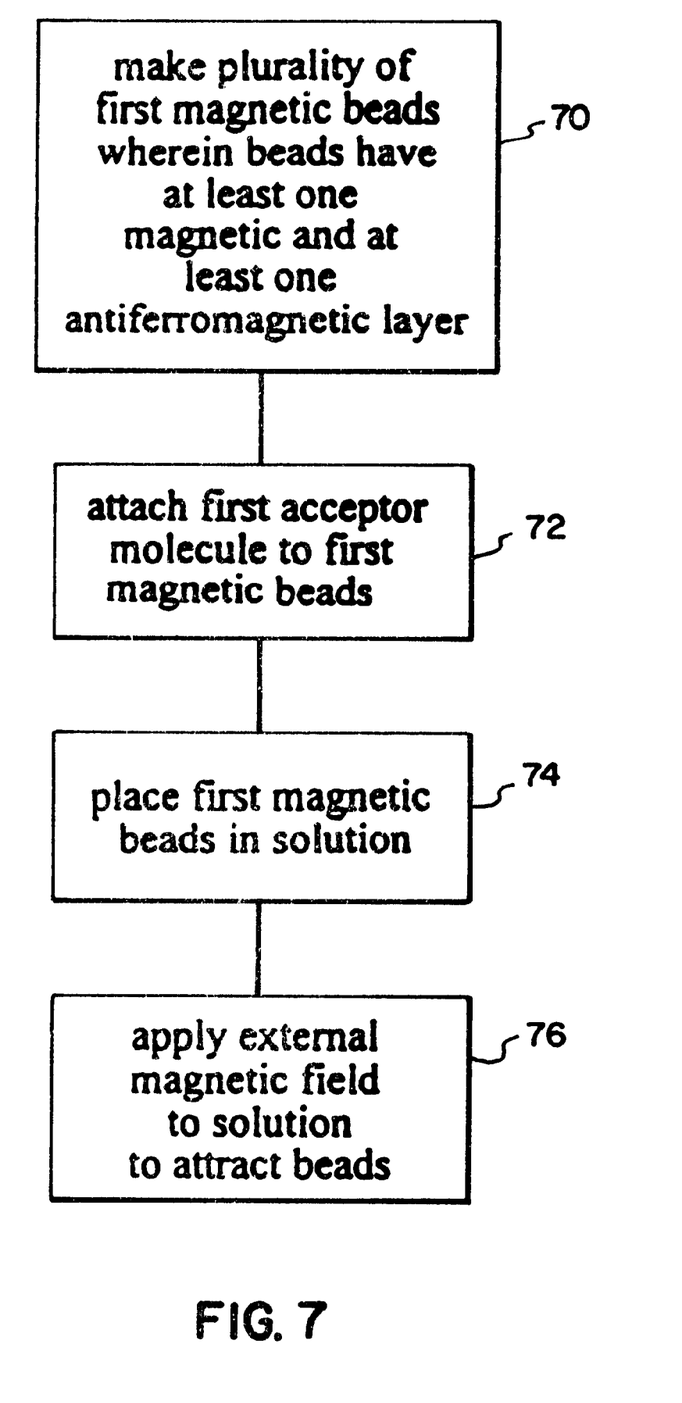
FIG. 7 illustrates the method steps used in practicing the present invention.

FIG. 7 illustrates the method steps used in practicing the present invention.

Block 70 illustrates the step of making a plurality of first magnetic beads having a first magnetic moment, the first magnetic beads having at least one magnetic layer and at least one antiferromagnetic layer.

Block 72 illustrates the step of attaching a first acceptor molecule to the first magnetic beads.

Block 74 illustrates the step of placing the first magnetic beads into a solution. Block 76 illustrates the step of applying an external magnetic field to the solution, hereby the first magnetic beads are attracted to a source of the magnetic field.

Attachment and Use of Affinity Recognition Molecules Bound to Magnetic Particles The following sections discuss the use of the above identified magnetic particles as nuclei for affinity molecules that are bound to the magnetic particles of the present invention. As indicated above, magnetic particles according to the present invention are attached to at least one affinity recognition molecule. As used herein, the term "affinity recognition molecule" refers to a molecule that recognizes and binds another molecule by specific three-dimensional interactions that yield an affinity and specificity of binding comparable to the binding of an antibody with its corresponding antigen or an enzyme with its substrate. Typically, the binding is noncovalent, but the binding can also be covalent or become covalent during the course of the interaction. The noncovalent binding typically occurs by means of hydrophobic interactions, hydrogen bonds, or ionic bonds. The combination of the affinity recognition molecule and the molecule to which it binds is referred to generically as a "specific binding pair." Either member of the specific binding pair can be designated the affinity recognition molecule; the designation is for convenience according to the use made of the interaction. One or both members of the specific binding pair can be part of a larger structure such as a virion, an intact cell, a cell membrane, or a subcellular organelle such as a mitochondrion or a chloroplast.

Examples of affinity recognition molecules in biology include antibodies, enzymes, specific binding proteins, nucleic acid molecules, and receptors. Examples of receptors include viral receptors and hormone receptors. Examples of specific binding pairs include antibody-antigen, antibodyhapten, nucleic acid molecule-complementary nucleic acid molecule, receptor-hormone, lectin-carbohydrate moiety, enzyme substrate, enzyme-inhibitor, biotin-avidin, and viruscellular receptor. One particularly important class of antigens is the Cluster of Differentiation (CD) antigens found on cells of hematopoietic origin, particularly on leukocytes, as well as on other cells. These antigens are significant in the activity and regulation of the immune system. One particularly significant CD antigen is CD34, found on stem cells. These are totipotent cells that can regenerate all of the cells of hematopoietic origin, including leukocytes, erythrocytes, and platelets.

As used herein, the term "antibody" includes both intact antibody molecules of the appropriate specificity and antibody fragments (including Fab, F(ab'), Fv, and F(ab')2 fragments), as well as chemically modified intact antibody molecules and antibody fragments such as Fv fragments, including hybrid antibodies assembled by in vitro reassociation of subunits. The term also encompasses both polyclonal and monoclonal antibodies. Also included are genetically engineered antibody molecules such as single chain antibody molecules, generally referred to as sFv. The term "antibody" also includes modified antibodies or antibodies conjugated to labels or other molecules that do not block or alter the binding capacity of the antibody.

As used herein, the terms "nucleic acid molecule," "nucleic acid segment" or "nucleic acid sequence" include both DNA and RNA unless otherwise specified, and, unless otherwise specified, include both double-stranded and single stranded nucleic acids. Also included are hybrids such as DNA-RNA hybrids. In particular, a reference to DNA includes RNA that has either the equivalent base sequence except for the substitution of uracil and RNA for thymine in DNA, or has a complementary base sequence except for the substitution of uracil for thymine, complementarity being determined according to the Watson-Crick base pairing rules. Reference to nucleic acid sequences can also include modified bases or backbones as long as the modifications do not significantly interfere either with binding of a ligand such as a protein by the nucleic acid or with Watson-Crick base pairing.

Methods for the covalent attachment of biological recognition molecules to solid phase surfaces, including the magnetic particles of the present invention, are well known in the art and can be chosen according to the functional groups available on the biological recognition molecule and the solid phase surface.

Many reactive groups on both protein and non-protein compounds are available for conjugation.

For example, organic moieties containing carboxyl groups or that can be carboxylated can be conjugated to proteins via the mixed anhydride method, the carbodiimide method, using dicyclohexylcarbodiimide, and the N hydroxysuccinimide ester method.

If the organic moiety contains amino groups or reducible nitro groups or can be substituted with such groups, conjugation can be achieved by one of several techniques. Aromatic amines can be converted to diazonium salts by the slow addition of nitrous acid and then reacted with proteins at a pH of about 9. If the organic moiety contains aliphatic amines, such groups can be conjugated to proteins by various methods, including carbodiimide, tolylene-2,4-diisocyanate, or malemide compounds, particularly the N-hydroxysuccinimide esters of malemide derivatives. An example of such a compound is 4(Nmaleimidomethyl)-cyclohexane-1-carboxylic acid. Another example is m-male imidobenzoyl-N-hydroxysuccinimide ester. Still another reagent that can be used is N-succinimidyl-3 (2-pyridyldithio) propionate. Also, bifunctional esters, such as dimethylpimelimidate, dimethyladipimidate, or dimethylsuberimidate, can be used to couple amino-group containing moieties to proteins.

Additionally, aliphatic amines can also be converted to aromatic amines by reaction with p-nitrobenzoylchloride and subsequent reduction to a p-aminobenzoylamide, which can then be coupled to proteins after diazotization.

Organic moieties containing hydroxyl groups can be cross-linked by a number of indirect procedures. For example, the conversion of an alcohol moiety to the half ester of succinic acid (hemisuccinate) introduces a carboxyl group available for conjugation. The bifunctional reagent sebacoyldichloride converts alcohol to acid chloride which, at pH 8.5, reacts readily with proteins. Hydroxyl containing organic moieties can also be conjugated through the highly reactive chlorocarbonates, prepared with an equal molar amount of phosgene.

For organic moieties containing ketones or aldehydes, such carbonyl-containing groups can be derivatized into carboxyl groups through the formation of O-(carboxymethyl) oximes. Ketone groups can also be derivatized with p-hydrazinobenzoic acid to produce carboxyl groups that can be conjugated to the specific binding partner as described above. Organic moieties containing aldehyde groups can be directly conjugated through the formation of Schiff bases which are then stabilized by a reduction with sodium borohydride.

One particularly useful cross-linking agent for hydroxyl-containing organic moieties is a photosensitive noncleavable heterobifunctional cross-linking reagent, sulfosuccinimidyl 6-[4¢-azido-2¢-nitrophenylamino] hexanoate. Other similar reagents are described in S. S. Wong, "Chemistry of Protein Conjugation and CrossLinking," (CRC Press, Inc., Boca Raton, Fla. 1993). Other methods of crosslinking are also described in P. Tijssen, "Practice and Theory of Enzyme Immunoassays" (Elsevier, Amsterdam, 1985), pp. 221–295.

Other cross-linking reagents can be used that introduce spacers between the organic moiety and the biological recognition molecule. The length of the spacer can be chosen to preserve or enhance reactivity between the members of the specific binding pair, or, conversely, to limit the reactivity, as may be desired to enhance specificity and inhibit the existence of cross-reactivity.

Although, typically, the biological recognition molecules are covalently attached to the magnetic particles, alternatively, noncovalent attachment can be used. Methods for noncovalent attachment of biological recognition molecules to magnetic particles are well known in the art and need not be described further here.

Conjugation of biological recognition molecules to magnetic particles is described in U.S. Pat. No. 4,935,147 to Ullman et al., and in U.S. Pat. No. 5,145,784 to Cox et al., both of which are incorporated herein by this reference.

Applications of Magnetic Particles According to the Present Invention

Magnetic particles according to the present invention can be used in many applications, both analytical and preparative. Among the analytical applications are specific binding assays such as immunoassays. Magnetic particles according to the present invention that have attached to them an antibody or other biological recognition molecule can be used in many types of immunoassays. Protocols for performing such immunoassays are well known in the art and need not be described in detail here. However, immunoassays are of two general types, sandwich and competitive. Typically, in sandwich immunoassays, a labeled antibody is used and what is detected is a ternary complex of an unlabeled antibody that is generally immobilized on a solid phase, the antigen, and a labeled antibody that also binds to the antigen. For performance of a sandwich immunoassay with magnetic beads according to the present invention, the unlabeled antibody is attached to the magnetic beads, and a labeled antibody is used. The labeled antibody can be labeled with an enzyme label, a fluorescent label, a chemiluminescent label, a bioluminescent label, a radioactive label, a dye label, a colloidal metal label, or any other label known to the art. Typically, in competitive immunoassays, the antigen or hapten to be assayed is mixed with antibody on a solid support and with a defined quantity of labeled analyte or analyte analogue. The unlabeled antigen or hapten in the sample competes with the labeled antigen or hapten for binding to the antibody on the solid support. Magnetic particles according to the present invention can be used as the solid support to which the antibody is bound. The magnetic particles are then separated from the mixture of the antibody, the particles, and the labeled component by application of magnetic force, and the presence or quantity of label associated with the magnetic particles is then determined in order to detect or determine the analyte. Various conventional washing steps can be incorporated into the procedure to reduce the background and improve the reproducibility of the immunoassay.

The foregoing discussion is intended to be illustrative rather than exhaustive, and many variations on these assay formats exist. Immunoassays employing magnetic particles are described in U.S. Pat. No. 4,935,147 to Ullman et al., and in U.S. Pat. No. 5,145,784. Magnetic particles according to the present invention that have a biological recognition marker on their surfaces can also be used for preparative purposes, i.e., for isolation and purification of a component that is bound specifically by the biological recognition molecule. Typically, the preparative procedure involves the following steps:

(1) contacting the magnetic particles with a mixture that contains the component in a suspension so that the component can be bound by the magnetic particles;

(2) separating the magnetic particles from the suspension by the application of magnetic force; and (3) eluting the component from the magnetic particles to purify the component.

Typically, the component is eluted from the magnetic particles by methods that break the noncovalent bonds between the component and the biological recognition molecule on the magnetic particles. These methods include, but are not limited to, changes in pH, addition of salt, or addition of chaotropic agents such as guanidinium chloride or sodium dodecyl sulfate. These methods are well known in the art and need not be described further here.

The component to be isolated can be a protein, an antigen, a hapten, a virus, a receptor, a carbohydrate, a hormone, a membrane, an organelle, a bacterial cell, an animal cell, or any molecule or molecular assembly that is specifically bound by the biological recognition molecule. One particularly significant component to be isolated is immune system stem cells. These possess an antigen known as CD34 on their surface and can be selected and isolated by means of antibodies specific for that antigen. Immune system stem cells can be selected and isolated as a means of repopulating the immune system of a patient after extensive chemotherapy or radiation. The cells are isolated before the treatment and reinfused into the patient after the treatment. Preferably, a sufficient quantity of immune system stem cells is purified to repopulate the immune system of a patient who has previously undergone therapy killing the stem cells of the patient.

Conclusion

The magnetic particles of the present invention can be used for simultaneously performing multiple separations and purifications of different components, such as cells bearing different Cluster of Differentiation (CD) antigens. The simultaneous separations are performed in parallel. Other applications which exploit the unusual and controllable magnetic characteristics are also possible.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. A composition of matter comprising:

a magnetic particle comprising a first ferromagnetic layer having a moment oriented in a first direction, a second ferromagnetic layer having a moment oriented in a second direction generally antiparallel to said first direction, and a nonmagnetic spacer layer located between and in contact with the first and second ferromagnetic layers, and wherein the magnitude of the moment of the first ferromagnetic layer is substantially equal to the magnitude of the moment of the second ferromagnetic layer so that the magnetic particle has substantially zero net magnetic moment in the absence of an applied magnetic field, and wherein the thickness of the magnetic particle is substantially the same as the total thickness of said layers making up the particle;

a coating on the surface of the magnetic particle; and an affinity recognition molecule attached to the coating of the magnetic particle for selectively binding with a target molecule.

2. The composition of matter of claim 1 wherein the magnetic particle further comprises a first antiferromagnetic layer in contact with and exchange coupled with the first ferromagnetic layer for pinning the moment of the first ferromagnetic layer in said first direction.

3. The composition of matter of claim 2 wherein the magnetic particle further comprises a second antiferromagnetic layer in contact with and exchange coupled with the second ferromagnetic layer for pinning the moment of the second ferromagnetic layer in said second direction.

4. The composition of matter of claim 1 wherein the affinity recognition molecule is attached to the coating of the magnetic particle by covalent bonding.

5. The composition of matter of claim 1 wherein the affinity recognition molecule is selected from the group consisting of antibodies, antigens, lectins, hormones, enzymes and nucleic acids.

* * * * *